US00PP12918P2

(12) United States Plant Patent
Delbard

(10) Patent No.: US PP12,918 P2
(45) Date of Patent: Sep. 3, 2002

(54) SPRAY ROSE PLANT NAMED 'DELSPRABLA'

(75) Inventor: Guy Delbard, Hyeres (FR)

(73) Assignee: Société Anonyme des Pépiniéres et Roseraies Georges Delbard, Commentry (FR)

( * ) Notice: Subject to any disclaimer, the term of this patent is extended or adjusted under 35 U.S.C. 154(b) by 0 days.

(21) Appl. No.: 09/588,762

(22) Filed: Jun. 6, 2000

(30) Foreign Application Priority Data

Jan. 10, 2000 (FR) ..... 17059

(51) Int. Cl.[7] ..... A01H 5/00
(52) U.S. Cl. ..... Plt./103

(58) Field of Search ..... Plt./102, 103, 104, Plt./144, 145

*Primary Examiner*—Bruce R. Campell
*Assistant Examiner*—June Hwu
(74) *Attorney, Agent, or Firm*—Burns, Doane, Swecker & Mathis, L.L.P.

(57) ABSTRACT

A new and distinct variety of *Rosa hybrida* Spray rose plant is provided which abundantly forms clusters of attractive double flowers arranged as a spray which are mostly creamy-white and more yellow-white in the center. The plant is well suited for cut flower production under greenhouse growing conditions. The flowers are long lasting. The plant exhibits an upright to bushy growth habit, forms vigorous vegetation, and is well suited for greenhouse forcing for commercial rose production. Additionally, the plant is resistant to common rose plant diseases when grown under greenhouse growing conditions.

1 Drawing Sheet

SUMMARY OF THE INVENTION

The new variety of *Rosa hybrida* Spray rose plant was created by artificial pollination wherein two parents were crossed which previously had been studied in the hope that they would contribute the desired characteristics. The female parent (i.e., the seed parent) of the new variety was an unnamed rose seedling. The male parent (i.e., the pollen parent) of the new variety also was an unnamed rose seedling. The parentage of the new variety can be summarized as follows:

Unnamed Rose Seedling×Unnamed Rose Seedling.

The seeds resulting from the above pollination were sown and 265 small plantlets were obtained which were physically and biologically different from each other. Selective study resulted in the identification of a single plant of the new variety.

It was found through careful study that the new Spray roe variety of the present invention can be characterized by the following combination of characteristics:

(a) From a physical point of view it forms medium green mature wood, assumes an upright to bushy growth habit, and forms attractive long-lasting clusters of creamy-white double flowers that are more yellow-white in the center, and (b) From the biological point of view forms vigorous vegetation, produces flowers in abundance, exhibits the ability readily to be forced, and is resistant to common rose plant diseases when grown under greenhouse growing conditions.

The new variety well meets the needs of the horticultural industry and is particularly well suited for growing in the greenhouse for the commercial production of attractive clusters of cut flowers.

The new variety can be readily distinguished from other spray rose varieties in view of the combination of characteristics described herein. For instance, the well-known 'Interniki' (U.S. Plant Pat. No. 8,114) spray rose variety forms blossoms of a red coloration unlike the creamy-white blossoms of the new variety, displays a peduncle with much hairiness unlike the new variety, and displays florals stems and under leaflet surface of a lighter green coloration than the new variety. The new variety exhibits long and straight stems and commonly bears approximately 3 to 20 blossoms per cluster. When grown under cooler growing conditions the petals of the new variety can be bordered with light pink. The vase life of the mostly creamy-white cut flowers is long.

The new variety has been found to undergo asexual propagation and can be readily reproduced by conventional routes, such as budding (i.e., eye grafting). This asexual reproduction as performed in the South of France has demonstrated that the characteristics of the new variety are strictly transmissible from one generation to another and are firmly fixed.

The new variety has been named the 'Delsprabla' variety.

BRIEF DESCRIPTION OF THE PHOTOGRAPH

The accompanying photograph shows as nearly true as it is reasonably possible to make the same in a color illustration of this character typical specimens of the plant parts of the new variety when growing in greenhouses in the South of France. The plants were approximately eleven months of age and were observed during March, 2000.

FIG. 1—illustrates a specimen of a flowering stem;

FIG. 2—illustrates a specimen of a main branch;

FIG. 3—illustrates a specimen of a young shoot with numerous buds in various stages of opening and a fully open flower;

FIG. 4—illustrates a specimen of a young shoot where primarily foliage is shown;

FIG. 5—illustrates from left to right specimens of a leaf with 7 leaflets—plan view—under surface; a leaf with 7 leaflets—plan view—upper surface; a leaf with 5 leaflets— plan view—upper surface; and a leaf with 3 leaflets—plan view—upper surface;

FIG. 6—illustrates from top to bottom specimens of a pair of fully open flowers—plan view—obverse (left) and—plan view—reverse (right); a pair of open flowers—plan view—obverse (left) and —plan view—reverse (right); a pair of flowers in the course of opening; a pair of newly opened flowers; and a pair of floral buds at the opening of the sepals (left) and a pair of floral buds at the opening of the petals (right); and FIG. 7—illustrates specimens of a floral receptacles showing the arrangement of the stamens and pistils (left) and a floral receptacle showing the arrangement of the pistils with the stamens removed (right).

DETAILED DESCRIPTION

The chart used in the identification of the colors is that of The Royal Horticultural Society (R.H.S. Colour Chart). The description is based on the observation of plants grown in greenhouses in the South of France. The plants were approximately eleven months of age and were observed during March, 2000. The coloration in common terms sometimes also is provided.

Class: Spray Rose

Plant:

*Height.*—Plants which were pruned at a height of 1 m commonly produce floral stems having a length of approximately 40 to 80 cm (approximately 60 cm on average).

*Habit.*—Upright to bushy.

*Width.*—Approximately 60 to 70 cm.

Branches:

*Color.*—Young shoots: when approximately 20 cm in length, Yellow-Green Group 146C, and with some bronze where exposed to sunlight. Floral stems: Medium green, Yellow-Green Group 146B and 146C. Mature wood: Darker medium green, Yellow-Green Group 146A.

*Thorns.*—Configuration: Upper edge: flat to slightly concave. Under edge: concave to deeply concave. Quantity: Short prickles typically are absent, and long prickles as indicated hereafter on 60 cm of stem commonly number approximately 16. Length: approximately 11 mm on average on floral stems and approximately 9 mm on average on mature wood, and commonly range from about 8 to 14 mm in each instance. Color: on a young shoots approximately 30 cm long, Greyed-Purple Group 184B and 184C; on floral stems Greyed-Yellow Group 161C; and on mature wood, Greyed-Orange Group 165A and 165B.

*Leaves.*—Number: typical for the class. Size: medium, and commonly measure approximately 7.5 to 14 cm in length and approximately 8 to 11 cm in width. Stipules: adnate, approximately 10 to 15 mm in length, approximately 4 to 5 mm (average close to approximately 5 mm) in width at the mid-point, and approximately 5 to 7 mm (average approximately 6.5 mm) in width at the distal extremity, and normal for the class.

*Leaflets.*—Number: commonly 3 to 7, on a 60 cm length stem one commonly observes 1 three leaflet, 4 five leaflets, and 6 seven leaflets. Size: medium. Shape: the base of the terminal leaflet is obtuse to rounded and slightly convex in cross section. Serration: present, medium, deep, and irregular. General appearance: consistent, medium glossy. Petiole: the inner surface is grooved and commonly lacking a glandular edge. Petiole color on young shoot: Greyed-Purple Group 184A on inner surface and at the base with some bronze on the outer surface. Petiole color on floral stem: Yellow-Green Group 146A commonly with a tiny bronze line around the petiole on the inner surface and Yellow-Green Group 146C with bronze on the outer surface. Petiole color on mature wood: Yellow-Green Group 146A on inner surface and Yellow-Green Group 146C on outer surface. Petiole length of terminal leaflet: approximately 16 to 22 mm, (average 18 mm with a standard deviation of 2 mm). Terminal leaflet length: approximately 42 to 62 mm (average approximately 57 mm with a standard deviation of 3 mm). Terminal leaflet width: approximately 28 to 41 mm (average approximately 37 mm with a standard deviation of 3 mm). Terminal leaflet shape at base: obtuse to rounded. Terminal leaflet shape of apex: cuspidate. Leaflet color of young shoot: Yellow-Green Group 147A with purple serrations on upper surface and Greyed-Purple Group 183C and a blend of Yellow-Green Group 152A and Greyed-Purple Group 183C on under surface. Leaflet color on floral stem: Yellow-Green Group 147A on upper surface and under surfaces with glossiness of upper surface. Leaflet color of mature wood: Yellow-Green Group 147A on upper surface and Yellow-Green Group 147B on under surface.

Inflorescence:

*Number of flowers.*—Generally approximately 3 to 20 per stem in a cluster. Under greenhouse growing conditions it is most common to have approximately 10 flowers per stem.

*Peduncle.*—Yellow-Green Group 146B, slightly hairy, perfumed, and erect at the beginning of flowering and with some bending when the flowers are fully open. The length commonly is approximately 57 mm for the central flower at the time of harvest.

*Sepals.*—Configuration: elongated and sharply pointed as illustrated. There commonly is 1 with medium to strong extensions, 2 with weak extensions and 2 without extensions. The lengths commonly average approximately 23 to 32 mm. Color: Yellow-Green Group 146D on the upper surface commonly with a white line on the edge, and Yellow-Green Group 146A and 146B on the under surface.

*Buds.*—Shape: ovate in longitudinal section just prior to the opening of the sepals. Size before calyx breaks: approximately 20 to 25 mm (approximately 22 mm on average). Color as calyx breaks: pale yellow, Yellow Group 4C with traces of pink, Red Group 54D. Size as first petals of second row open: approximately 28 to 32 mm (average approximately 30 mm). Color as the first petals of second row open: the inside coloration is pale yellow, Yellow Group 4D at the base and whiter in the middle, and White Group 155B at the edge, and the outside coloration is pale yellow, Yellow Group 4C at the base, becoming whiter in the middle and White Group 155A at the edge. The petal edges can display some light pink, Red Group 62A under cool growing conditions.

*Flower.*—Time: in a greenhouse at a temperature of 16 to 25° C. the plant commonly blooms approximately 53 days during the winter. Shape: double and as a spray. Form: when viewed from above round to irregularly rounded, and when viewed from the side flattened convex. Diameter: medium to large, approximately 54 to 66 mm (approximately 62 mm on average with a standard deviation of 3 mm). Petal number: commonly approximately 24 to 36 (approximately 30 on average). Petal size (second row from outside): the length is approximately 28 to 30 mm (approximately 29 mm on average with a standard deviation of 1 mm), and the width is approximately 24 to 31 mm (approximately 28 mm on average with a standard deviation of 2 mm). Petal shape: the first row of petals commonly exhibits a large obovate configuration with weak to medium margin undulation, and strong reflexing at the margin. The petal apex is rounded and the petal base is intermediate rounded and obtuse. Petal color: the petals at the center are near Yellow Group 4C and 4D and Yellow Group 4B at the base, the petals from the second row from the outside are White Group 155D on both surfaces. In colder weather pink sometimes is present on the edges of the petals. Petal spot at base: Size: approximately 4 mm. Color spot inner side: pale yellow, Yellow Group 4C. Color spot outer side: pale yellow, Yellow Group 4D. Petaloids: a few petaloids (e.g., 2 to 3 per bloom) commonly are present and may be fused to the stamens. They commonly are arched in configuration and possess a smooth texture. The size varies considerably. They commonly are 5 to 15 mm in length and 3 to 6 mm in width. Stamens: approximately 80 in number and are somewhat regularly arranged about the same levels as the pistils. Filaments: located regularly around and slightly above the pistils, approximately 5 mm in length, and the color is Yellow Group 13B and 13C. Anthers: approximately 1.5 mm in length and approximately 1 mm in width, and Yellow-Orange Group 21B in coloration. Pollen: normal in quantity for the class and Yellow-Orange Group 15A in coloration. Pistils: approximately 30 to 70 (*60* on average). Styles: approximately 7 mm in length and pale yellow, Yellow Group 2D, in coloration. Stigmas: Yellow Group 4C, and generally present at about the same level as the anthers. Receptacle: in longitudinal sectional configuration in the shape of a pitcher and at the open flower stage approximately 9 mm in length on average and approximately 7 mm in width on average. The coloration is Yellow-Green Group 144A. Hips: Orange Group 28A in coloration, and commonly are approximately 16 to 17 mm in diameter. Seeds: Yellow Group 12D in coloration, medium in size, and approximately 8 to 12 in number (approximately 10 on average). Petal drop: petals detach cleanly. Fragrance: none, except for the fragrance of the hairy peduncle which commonly is apparent upon touching. Lasting quality: long with the flowers commonly lasting approximately 8 days when cut and placed in a vase.

Development:

*Vegetation.*—Vigorous.

*Blooming.*—Abundant, substantially continuous under greenhouse growing conditions.

*Resistance to forcing.*—Good.

*Resistance to diseases.*—Good with respect to Powdery Mildew, Downy Mildew and Botrytis under greenhouse conditions.

I claim:

1. A new and distinct variety of Spray rose plant characterized by the following combination of characteristics:

(a) From a physical point of view it forms medium green mature wood, assumes an upright to bushy growth habit, and forms attractive long-lasting clusters of creamy-white double flowers that are more yellow-white in the center, and (b) From the biological point of view forms vigorous vegetation, produces flowers in abundance, exhibits the ability readily to be forced, and is resistant to common rose plant diseases when grown under greenhouse growing conditions;

substantially as herein shown and described.

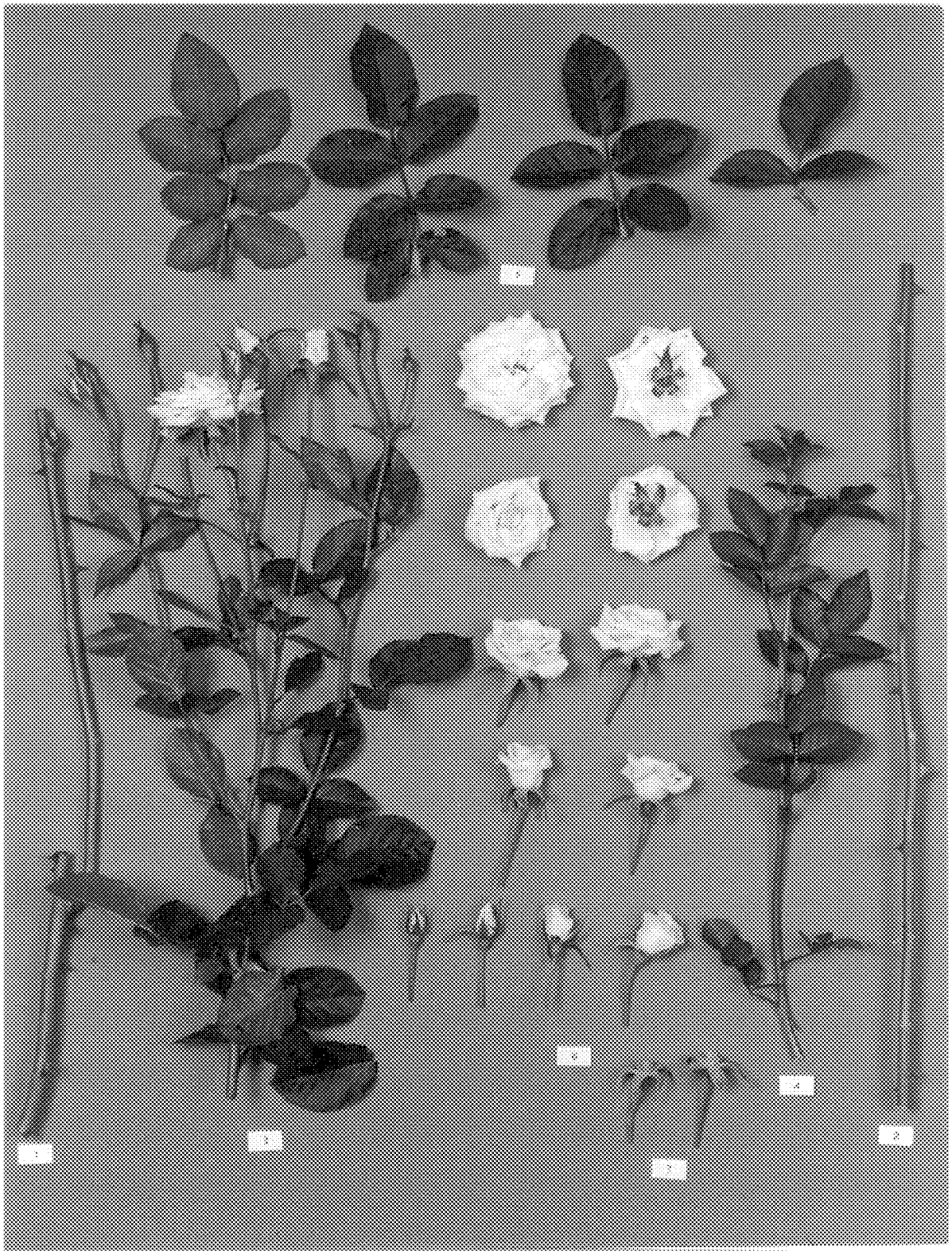

* * * * *